United States Patent
Matusch

(10) Patent No.: US 8,398,585 B2
(45) Date of Patent: Mar. 19, 2013

(54) INJECTOR AND TWO-CHAMBER SYSTEM HAVING SEALING CONTAINER ADAPTER

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 167 days.

(21) Appl. No.: 13/066,277

(22) Filed: Apr. 11, 2011

(65) Prior Publication Data

US 2011/0196292 A1    Aug. 11, 2011

Related U.S. Application Data

(63) Continuation-in-part of application No. PCT/EP2009/006996, filed on Sep. 29, 2009.

(30) Foreign Application Priority Data

Oct. 31, 2008   (DE) .......................... 10 2008 054 128

(51) Int. Cl.
*A61M 37/00* (2006.01)
(52) U.S. Cl. ................ 604/89; 604/82; 604/91
(58) Field of Classification Search ............... 604/82–92
See application file for complete search history.

(56) References Cited

U.S. PATENT DOCUMENTS

| 3,610,297 A | 10/1971 | Raaf et al. |
| 4,048,999 A * | 9/1977 | Kobel ............................. 604/90 |
| 2008/0306439 A1 * | 12/2008 | Nelson et al. ................... 604/84 |
| 2010/0262125 A1 | 10/2010 | Matusch |

FOREIGN PATENT DOCUMENTS

| CA | 2356614 A1 | 4/2000 |
| DE | 66 07 420 U | 2/1971 |
| DE | 36 18 158 A1 | 12/1987 |
| DE | 690 03 805 T2 | 5/1991 |
| EP | 0 882 441 A2 | 9/1998 |

* cited by examiner

*Primary Examiner* — Nicholas Lucchesi
*Assistant Examiner* — Leah Stohr
(74) *Attorney, Agent, or Firm* — R. S. Lombard; K. Bach

(57) ABSTRACT

The invention relates to a single-use injector and to a two-chamber system, wherein at least one first chamber is part of a cylinder-piston unit that can be received in the single-use injector, and wherein the second chamber is part of a container having at least one opening, and closed at least intermittently by means of a stopper and place in a container adapter releasably supported on the single-use injector. To this end, the stopper and the container adapter can be permanently latched to each other. When the container is inserted, the container adapter closes off the opening and displaces the stopper. When the container is inserted into the container adapter, the adapter connects the interior of the cylinder-piston unit to the interior of the container. By means of the present invention, a single-use injector and a two-chamber system having a reduced number of components is developed.

19 Claims, 6 Drawing Sheets

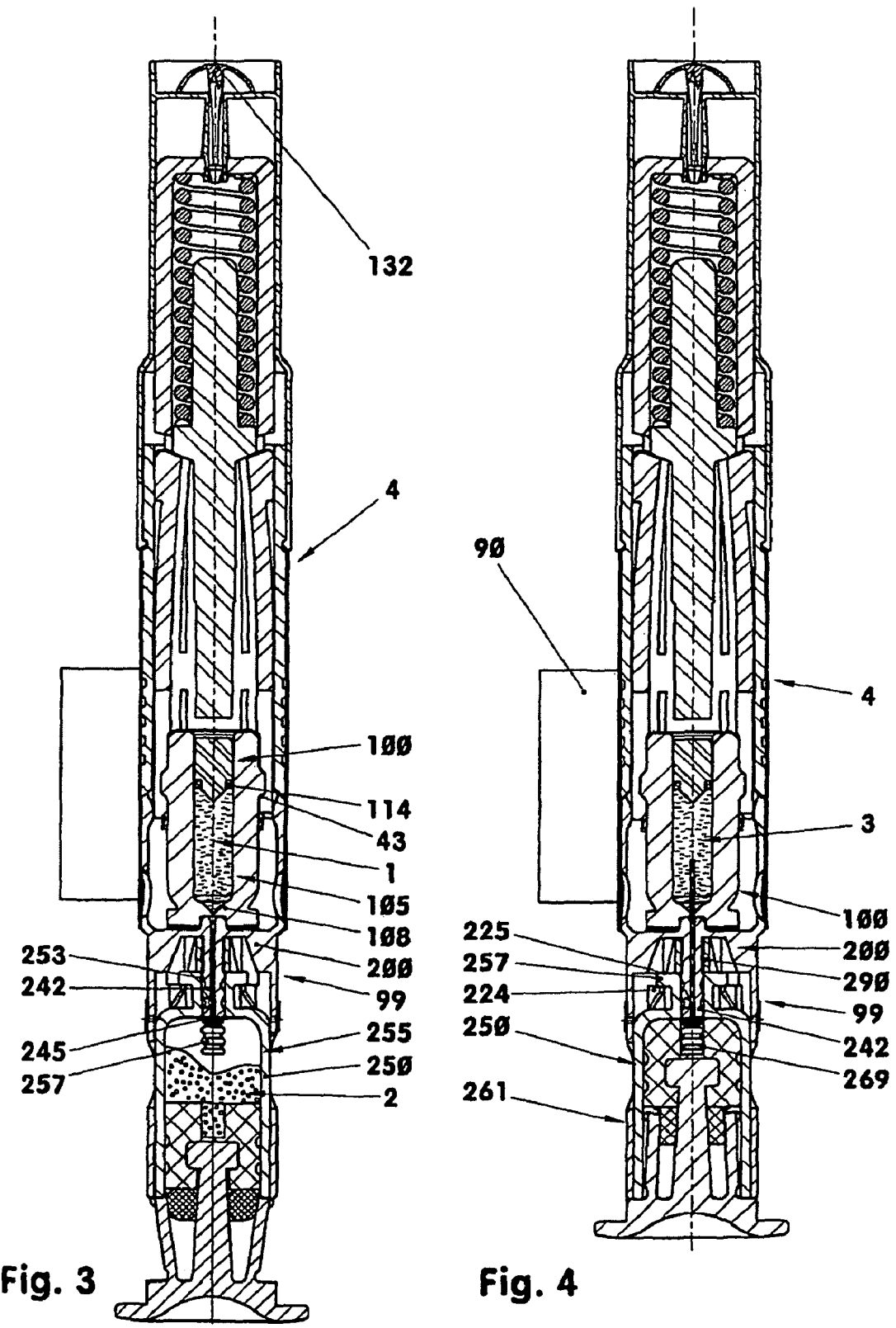

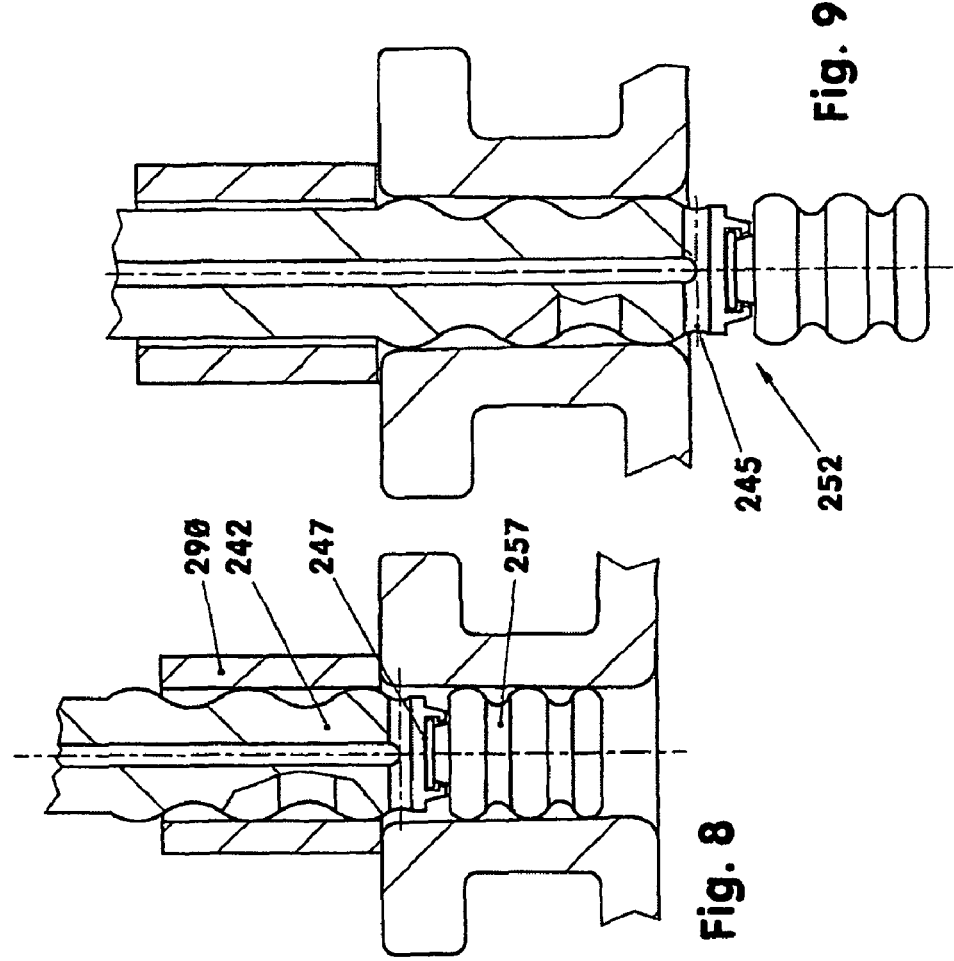
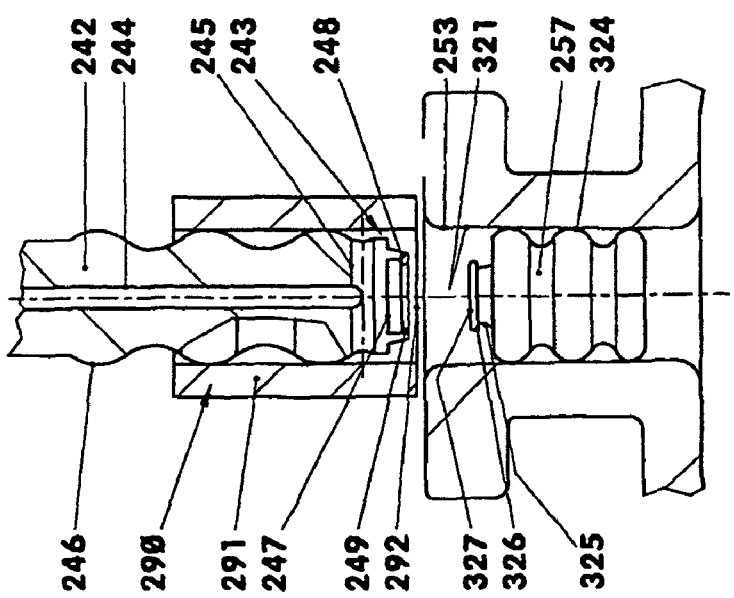
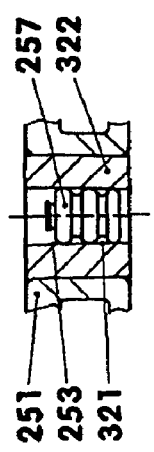

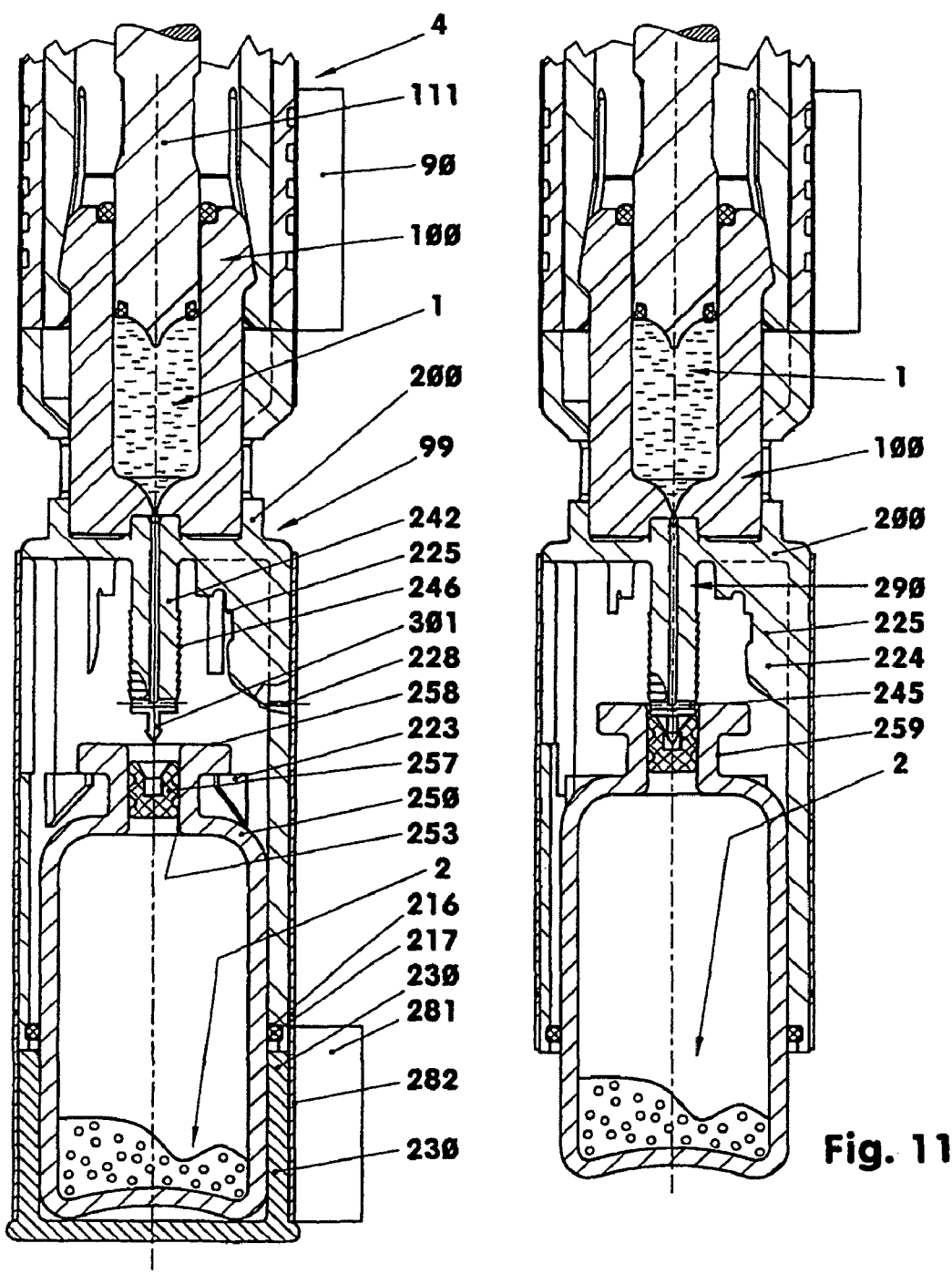

US 8,398,585 B2

INJECTOR AND TWO-CHAMBER SYSTEM HAVING SEALING CONTAINER ADAPTER

CROSS-REFERENCE TO RELATED APPLICATION

This is a continuation-in-part application of pending international application PCT/EP2009/006996 filed Sep. 29, 2009 and claiming priority of German Application No. 10 2008 054 128.1 filed Oct. 31, 2008.

BACKGROUND OF THE INVENTION

The invention relates to a single-use injector and a two-chamber system, at least a first chamber being part of a cylinder/piston unit which can be received in the single-use injector and the second chamber being part of a container having at least one opening, which container is closed at least temporarily by means of a stopper and is inserted in a container adapter which is detachably mounted on the single-use injector.

A single-use injector of this type and a two-chamber system are known, for example, from the subsequently published DE 10 2008 003 103 A1. A double adapter inserted into the container adapter pushes the stopper out of the opening such that the stopper falls into the container.

The present invention is therefore based on the problem of developing a single-use injector and a two-chamber system having a reduced number of components.

SUMMARY OF THE INVENTION

The invention relates to a single-use injector and to a two-chamber system, wherein at least one first chamber is part of a cylinder-piston unit that can be received in the single-use injector, and wherein the second chamber is part of a container having at least one opening, and closed at least intermittently by means of a stopper and placed in a container adapter releasably supported on the single-use injector. To this end, the stopper and the container adapter can be permanently latched to each other. When the container is inserted, the container adapter closes off the opening and displaces the stopper. When the container is inserted into the container adapter, the adapter connects the interior of the cylinder-piston unit to the interior of the container. By means of the present invention, a single-use injector and a two-chamber system having a reduced number of components is developed.

BRIEF DESCRIPTION OF THE DRAWINGS

Further details of the invention emerge from the schematically illustrated embodiments, shown in the following drawings, in which:

FIG. 3 shows the single-use injector after the container has been inserted;

FIG. 4 shows the single-use injector after the transfer by pumping;

FIG. 7 shows a detail from FIG. 1;

FIG. 8 shows a detail from FIG. 2;

FIG. 9 shows a detail from FIG. 3;

FIG. 10 shows a detail of a single-use injector and two-chamber system with a cylinder/piston unit;

FIG. 11 shows FIG. 10 during insertion of the container;

FIG. 15 shows the container with a closure insert.

DETAILED DESCRIPTION OF THE PARTICULAR EMBODIMENTS

Figure 1:
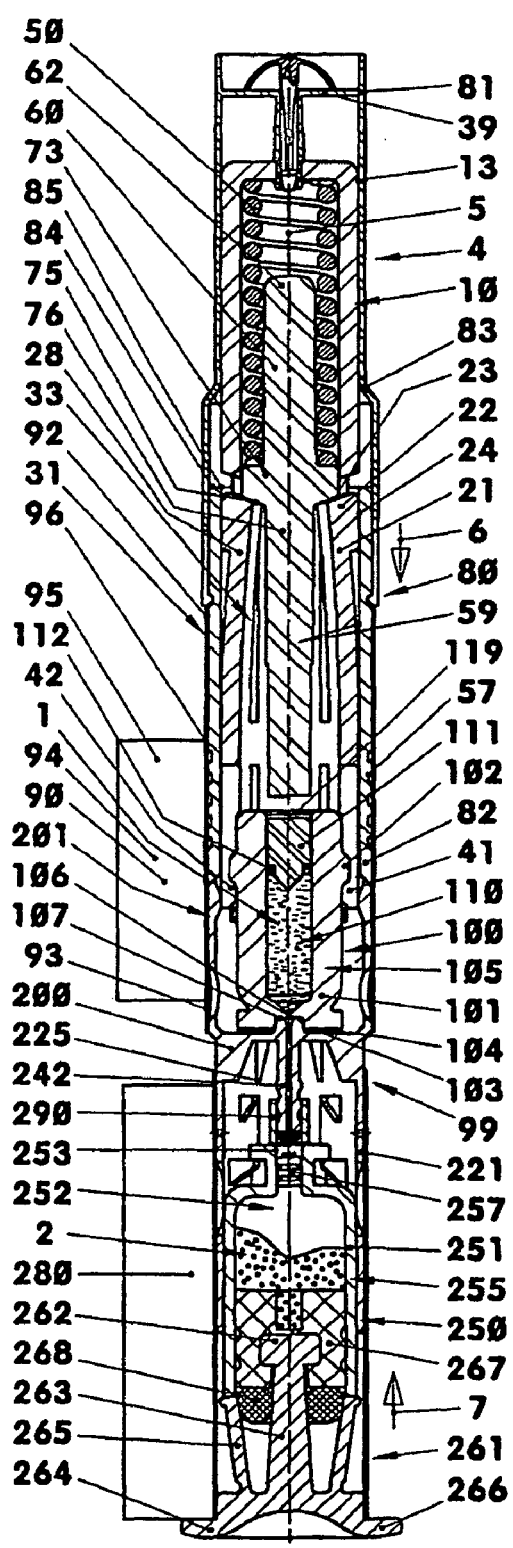
FIG. 1 shows a single-use injector and two-chamber system.

FIGS. 1-5 show a single-use injector (4) and a two-chamber system (99) adapted thereto. FIG. 1 shows, for example, the state of delivery to the user, in which the two-chamber system (99) is integrated in the single-use injector (4) and the single-use injector (4) is pre-tensioned. The first chamber (105) is, for example, partially filled with solvent (1) and the second chamber (255) is, for example, partially filled with lyophilisate (2). Both chambers (105, 255) are separated from each other.

Figure 2:
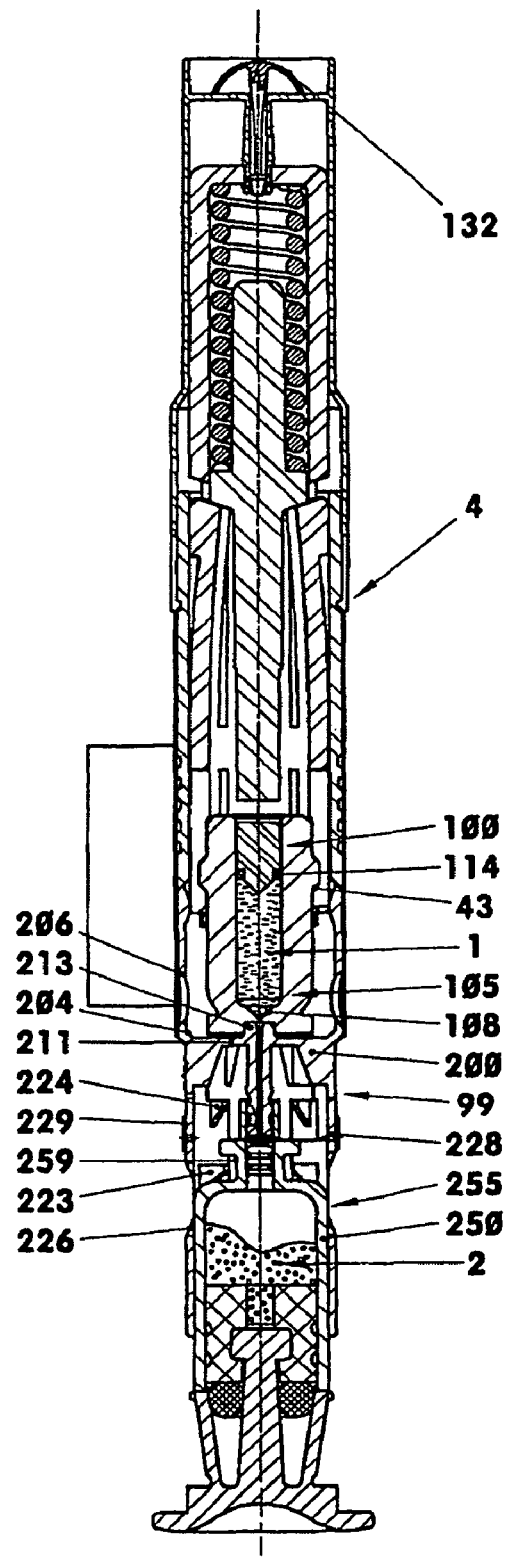
FIG. 2 shows the single-use injector and partially inserted container.

FIG. 2 shows an intermediate state in the connection of the two sterile chambers (105, 255). In FIG. 3, the two chambers (105, 255) are joined together to produce an injection solution (3).

Figure 5:
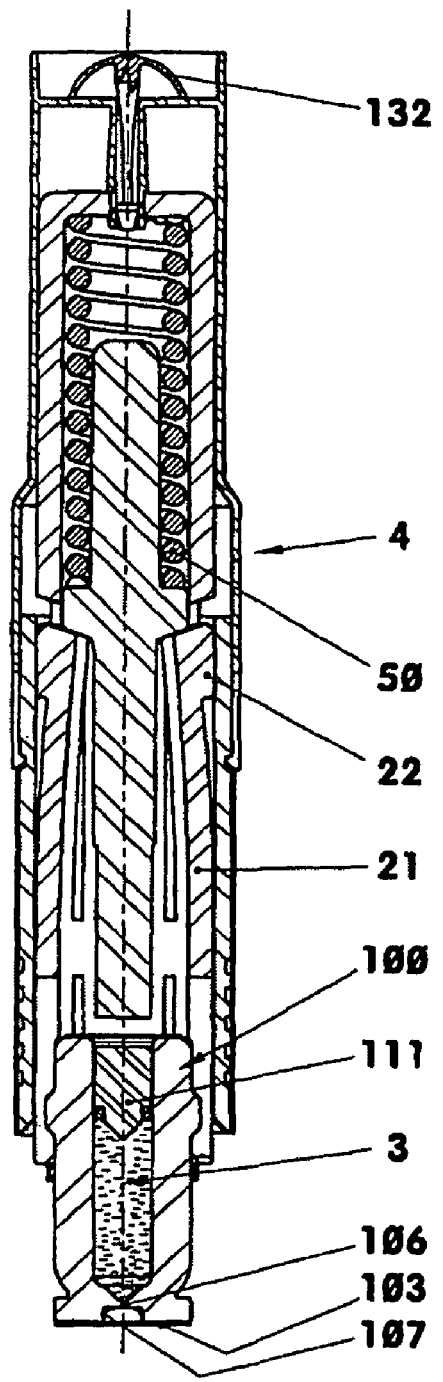
FIG. 5 shows the single-use injector with the cylinder/piston unit prior to triggering.
Figure 6:
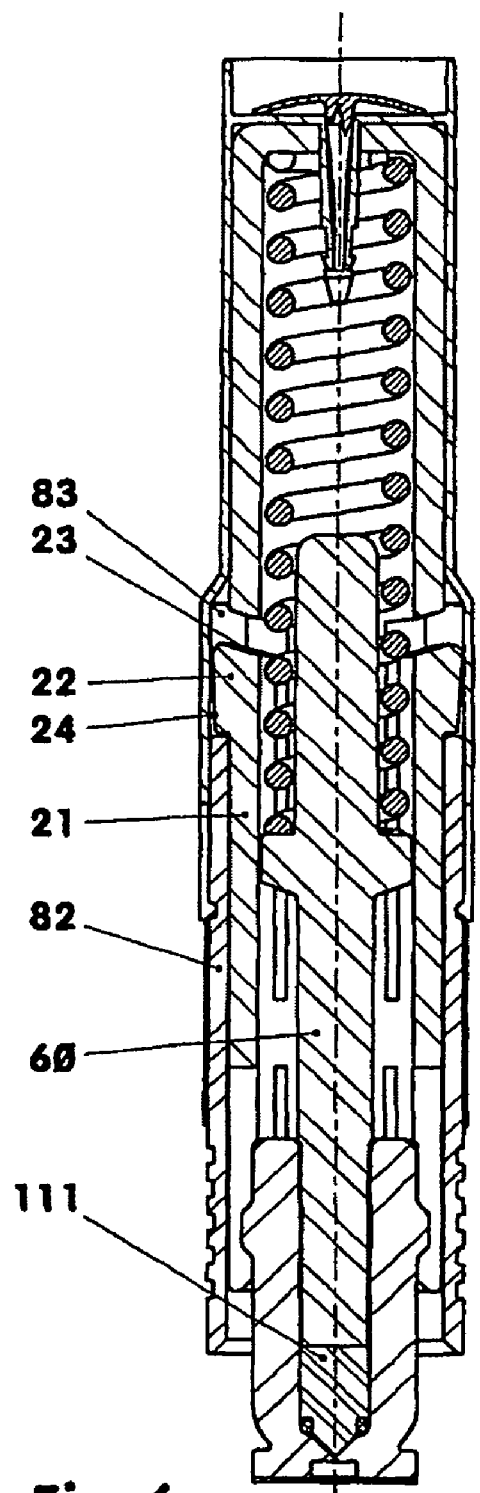
FIG. 6 shows FIG. 4 after triggering.

FIG. 4 shows the single-use injector (4) and the two-chamber system (99) after the production of the injection solution (3) and FIG. 5 shows this injector (4) with the injector-side chamber (105) prior to triggering. In the illustration of FIG. 6, the needleless single-use injector (4) is triggered and the injection solution (3) has been sprayed out.

The single-use injector (4) illustrated in FIGS. 1-6 comprises a housing (10), a piston actuating plunger (60) and a helical compression spring (50) as the spring energy store. In addition, a triggering unit (80) with a triggering element (82) and, in FIGS. 1-4, a securing element (90) are arranged on the housing (10).

The housing (10) is a one-piece, pot-shaped, downwardly open hollow body with an elevated floor (39). The housing is made, for example, from a glass fibre-reinforced polyamide by injection-moulding. The housing (10) has a substantially tubular form and is divided into two functional regions: on the one hand, the upper envelope region (31) and, on the other hand, the lower fixing region (41).

In the envelope region (31), the housing (10) has, for example, two mutually opposing, window-like apertures (33). A respective press rod (21), as a resilient bending bar, is moulded onto the lower edge of the individual aperture (33). The moulding-on site for the press rods (21) is positioned just above the fixing region (41). For forming each press rod (21), a narrow, at least roughly U-shaped gap, which surrounds the individual press rod (21) to the side and top, is located in the lower region of the envelope portion (31).

The press rod (21) has, for example over 80% of its length, the wall thickness and the curvature of the wall of the housing (10). This region has inter alia also the function of a resilient bending bar (28). It has a crescent-shaped cross section.

If appropriate, a portion of this bending bar (28) can also be equipped with a rectangular cross section in order to reduce bending stresses which occur during use in the edge region of the bending bar.

In the case of injectors in which the piston actuating plunger (60) is—at least in certain portions—guided straight with a low degree of play in the housing (10) and the piston actuating plunger (60) has sufficient bending strength, use may also be made of just a single press rod (21) instead of two or more press rods (21).

The—in this case—upper free end of the individual press rod (21) is formed by the radially outwardly protruding cam (22). The cam has at least one support surface (23) oriented in the direction of the centre line (5) and an abutment surface (24) facing away from the centre line (5).

The lower half of the housing (10) is surrounded by the sleeve-like triggering element (82). The triggering element is, for example, embodied in a substantially cylindrical manner and made, for example, of acrylonitrile butadiene styrene (ABS) copolymer. The triggering element (82) is longitudinally displaceably mounted on the radial outer surface (13) of the housing (10). It ends rearwardly with a sharp edge (85) which is part of an end-side, set-back flank (84) of the triggering element (82). According to FIG. 1, below the edge (85), the outward abutment surfaces (24) of the cams (22), which are moulded onto the press rods (21), touch the inner wall (59) of the triggering element (82) in a securing manner.

For example, close to the edge (85), a triggering cap (81), which completely surrounds the trailing end of the housing (10), is fastened to the triggering element (82). The triggering cap (81) comprises a peripheral widening (83) in which the cams (22) are received on triggering of the injector, cf. FIG. 6. In the case of a non-rotationally symmetrical triggering element (82), partial widenings or non-covered openings may also be present for each press rod (21), instead of this widening (83). Above the widening (83), the triggering cap (81) rests against the outer wall (13) of the housing (10) in a slidable manner.

The piston actuating plunger (60), which is arranged in the housing (10), is divided into two regions. The lower region is the piston slide (76). Its diameter is somewhat smaller than the internal diameter of the rear region of the cylinder (101) of a cylinder/piston unit (100). The lower end face of the piston slide (76) acts directly on the piston (111) of this cylinder/piston unit (100).

The upper region of the piston actuating plunger (60), the plunger plate (73), is a flat disc which is cylindrical at least in certain regions and the external diameter of which is smaller by a few tenths of a millimeter than the internal diameter of the housing (10) in the envelope region (31). The lower end side has a collar surface (75) which is arranged around the piston slide (76). The collar surface has the shape of a frustoconical envelope, the apex angle of which is approx. 100 to 140 degrees. In the illustrated exemplary embodiment, the collar surface (75) has an apex angle of 140 degrees. The notional apex of the frustoconical envelope rests on the centre line (5) in the region of the piston slide (76). The collar surface (75) can also be spherically curved.

Obviously, the piston slide (76) may also be embodied as a separate component in isolation from the plunger plate (73). For this purpose, the piston slide is then guided on the inner wall of the housing (10).

The helical compression spring (50) sits pre-tensioned between the plunger plate (73) and the elevated floor (39) of the housing (10). The helical compression spring (50) is supported on the floor (39) of the housing (10). The spring force of the helical compression spring (50) is transmitted to the press rods (21) via the plunger plate (73). Owing to the inclination of the collar surface (75), the press rods (21) are urged radially outward in the manner of a wedge gear. The triggering sleeve (82) permanently supports this radial force.

The piston actuating plunger (60) has a guide pin (62) above the plunger plate (73). The guide pin guides the helical compression spring (50) or is guided thereby. The piston slide (76) is located below the plunger plate (73), centrally in the extension of the guide pin (62).

The fixing region (41) for receiving the installable cylinder/piston unit (100), which comprises the first chamber (105), is located below the envelope portion (31). The fixing region (41) comprises, for example, eight spring hooks (42) oriented parallel to the centre line (5). The spring hooks (42) each have an at least two-flanked rear grip (43) for receiving the cylinder/piston unit (100) without play. The mutually opposing flanks of the rear grip (43) enclose an angle of, for example, 90 angular degrees. The length and the spring rate of the spring hooks (42) are designed in such a way that the cylinder/piston unit (100) can be installed without plastic deformation of the spring hooks (42).

In the exemplary embodiment, the cylinder/piston unit (100) consists of a transparent cylinder (101) which can be filled with water for injection purposes (1) or an injection solution (3). The water for injection purposes (1) can already contain active substances. In the illustration of FIG. 1, the piston (111) is in the rear position. Above the piston (111), the piston actuating plunger (60) is, for example, arranged in the housing (10) in such a way that, although it does not touch the piston (111), it is laterally guided by its lower end, for example in the upper region of the cylinder (101).

The cylinder (101) is, for example, a clearly visible, thick-walled pot, the optionally cylindrical outer wall of which carries a, for example peripheral, locking ring (102) which rests in a dimensionally stable manner against the flanks of the rear grip (43) of the spring hooks (42). The rodless piston (111) sits in the, for example cylindrical, hole of the cylinder (101). At its front, at least roughly conically configured end face, the piston (111) has an axial annular groove (112) for receiving a ring seal (114) or a permanently resilient sealing compound. A, for example cylindrical, metal plate is, if appropriate, embedded in the trailing end face of the piston (111).

A short, cylindrical, nozzle-like hole (106) is located at the centre of the hole of the cylinder (101), the cylinder floor of which is at least roughly adapted to the contour of the front piston end side. The diameter of the nozzle-like hole is approx. 0.1 to 0.5 millimeters. This hole (106) is one to five times as long as its diameter. It ends in a cylindrical recess (107) of the floor-side, outer end face (103) of the cylinder (101). In order to increase application safety, this send face (103) can additionally be provided with an adhesive ring (104).

The back of the cylinder (101) is closed in a sterile manner by a sterile filter membrane (119).

Furthermore, a container adapter (200) is inserted into the single-use injector (4). The container adapter is a bushing-like component which receives, for example, the second chamber (255)—the second chamber comprises in this case a container (250) embodied as a cylinder/piston unit (250)—in a container region (221). At the same time, the container adapter has a sleeve-like adapter region (201) with which it sits longitudinally displaceably in the housing (10).

The container adapter (200) is, for example, a single- or multi-part component which is elastically deformable at least in certain regions. In the case of a multi-part construction, the container adapter (200) may have regions of differing rigidity and elasticity. For example, the adapter region (201) may be designed to be elastically deformable and the container region (221) to be deformation-resistant.

The adapter region (201) is a cylindrical cup which surrounds at least the lower fifth of the cylinder (101) with a spacing. The adapter region has two mutually opposing, for example circular, windows (206) and an annular shoulder (204) on the intermediate floor (211). The windows (206) may be dispensed with if the container adapter material is transparent.

The container adapter (200) has, centrally in the intermediate floor (211), a transfer tube (242), which joins the adapter region (201) and the container region (221) together. For centering at the recess (107), the surface of the intermediate floor (211) facing the adapter region (201) has a central elevation (213). The minimum internal diameter of the transfer tube (242), the diameter of the hole (244), corresponds to at least the diameter of the nozzle-like hole (106). The minimum diameter of the hole (244) may be, for example, one millimeter. The diameter of the hole (244) can taper, for example conically, from both end sides toward the centre or from one end side toward the other. The transfer tube (242) has, for example, a maximum external diameter of 8 millimeters. In the illustration of FIG. 1, said transfer tube is formed cylindrically in the region adjacent to the intermediate floor (211) in the direction of the container region (221). Toward the tube end (243), cf. FIG. 7, the transfer tube (242) bears, for example, three bead-like, elastically deformable rings (246). In the undeformed state, the external diameter of said rings (246) is slightly larger than the diameter of the opening (253) of the container (250), and therefore the transfer tube (242), after insertion, tightly closes said opening (253).

In the illustration of FIGS. 1-7, the transfer tube (242) has, below the rings (246), a continuous transverse hole (245), the diameter of which, for example, corresponds to the diameter of the longitudinal hole (244) which is in the form of a blind hole. The transverse hole (245) is aligned with two at least approximately radially arranged slide recesses (228) in the, for example, cylindrical side wall of the container receptacle (221). The term "at least approximately" means in this case that the centre line of the hole can enclose an angle of up to 45 degrees with a radial line. Said slide recesses (228) are penetrated, for example during the manufacturing of the container adapter (200), by two slides which hold the transfer tube (242) and produce the transverse hole (245). The slide recesses (228) are covered, for example, by means of a valve hose (229).

The tube end (243) illustrated here has a, for example, central sliding surface (247) which is surrounded by a locking ring (248). The locking ring (248) has, for example, a peripheral locking lug (249) oriented inward. Instead of a locking ring (248), it is possible for, for example, three locking hooks which are each offset with respect to each other by 120 degrees of angle to be arranged on the end side of the transfer tube (242). The sliding surface (247) may also be arranged outside the locking ring (248) or outside the locking hooks. The end surface of the locking ring or a plane formed by the end surfaces of locking hooks may also form a sliding surface.

In the exemplary embodiment illustrated in FIGS. 1 and 7, a pot-shaped membrane cap (290) is firmly adhered to the end side, facing the container region (221), of the transfer tube (242). The membrane cap comprises a, for example cylindrical, elastically deformable wall region (291) and an end side embodied as a membrane (292). The membrane (292) can also be moulded onto the wall region (291). The wall thickness of the wall region (291) is, for example, one millimeter.

The container region (221) of the container adapter (200) has, for example, two groups of locking elements (223, 224) which are set apart from the intermediate floor (211) by different distances. The individual locking element (223, 224) is, for example, a triangular element protruding non-radially from the inner wall of the container region (221).

The cylinder/piston unit (250) is arranged in the container region (221). The external diameter of the cylinder/piston unit is just slightly smaller than the internal diameter of the container region (221).

The cylinder/piston unit (250) has a cylinder which is formed from a transparent tube (251), for example a glass or plastic material tube, such as cyclic olefin copolymer (COC), and a resilient stopper (257). In the illustration in FIGS. 1 and 2 and in the detail illustrations of FIGS. 7 and 8, the stopper (257) sits in the opening (253) of the container (250).

The opening (253) of the container (250), which is designed, for example, in the manner of a bottle, may be cylindrical or conical, wherein, in the case of a conical opening (253), the apex points in the direction of the container interior (252). At least the centrally oriented surface of the opening (253), the inner wall (321), has a higher surface hardness than the material of the inserted stopper (257), and therefore the sealing stopper (257) which is inserted into the opening (253) is elastically deformed.

The container opening (253) may be part of a closure insert (322), cf. FIG. 15. The inner wall (321) of the closure insert (322), which is produced, for example, from plastic may be, for example, ceramized.

On its, for example, cylindrical envelope surface, the stopper (257) has tyre-like beads (324) with which the stopper bears against the inner wall (321) in a sealing manner. On its upper side, the aperture-free stopper (257) has a, for example, conical attachment (325) which, in the exemplary embodiment illustrated, has a peripheral annular bead (326).

In the illustrations of FIGS. 1 and 7, the container (250) above the stopper (257) may optionally be additionally closed in a sterile manner by means of a membrane.

The back of the glass tube (251) is closed by a movable piston (261). The piston (261) consists of a piston rod (262), a rear piston pressure plate (264), a front stopper carrier (263) and a resilient piston stopper (267) placed thereover. In order to hold the piston (261) in its rear position when a vacuum has been created in the cylinder interior (252), the piston (261) additionally has two or more locking elements (265) which are, for example, moulded onto the piston pressure plate (264) and are—resiliently outwardly—supported on the rear edge of the glass tube (251). A resilient rubber ring (268), which presses the locking elements (265) outward, sits on the back of the piston stopper (267). On its front, the piston stopper (267) has, for example, a cylindrical recess (269).

The piston pressure plate (264) has, toward the glass tube (251), a cylindrical collar (266) which has the same external diameter as the container region (221).

In order to prevent triggering, the container adapter (200) is connected to the triggering element (82) of the injector via the banderole (90). The banderole (90) is a tamper-proof closure embodied as an adhesive label.

The banderole (90) itself is, for example, a strip of paper and/or film which is coated on one side with an adhesive in certain regions. The banderole consists of three separate strips which can each be separated from one another via a perforation (96) or via a different predetermined breaking point. The, in each case peripheral, perforations (96) are positioned above the slots (57) and below the windows (206).

According to FIG. 1, an unwinding banderole (280) is pasted over the container region (221) and the piston (261). The unwinding banderole (280) covers in this case the windows (226) and the locking elements (265) of the piston (261) in a protective manner. In addition, the unwinding film (280) prevents accidental extracting of the container adapter (200) from the housing (10).

During manufacture, the two cylinder/piston units (100, 250) are manufactured, for example, in separate production processes and filled on different production lines. The container adapter (200) is, for example, manufactured separately. The individual parts can thus be produced to stock and not be joined to the single-use injector until later. The components (1-3) are sterile and can be stored in a sterile manner. All the parts which may enter into contact with active substances and/or solvent are, for example, packaged in a sterile manner.

For packing—before delivery to the user—the first cylinder/piston unit (100) is, for example, inserted into the single-use injector (4) and interlocked. The container adapter (200) is also inserted into the single-use injector (4). In this case, for example, the membrane cap (290) remains on the transfer tube (242). The second cylinder/piston unit (250) is inserted into the container region (221) and interlocked with the locking hook (223) facing away from the intermediate floor (211). The stopper (257) closes the container opening (253) and does not touch the transfer tube (242).

In order to be able to use the single-use injector, the active substance (2), for example a lyophilisate, stored in the cylinder/piston unit (100) must be dissolved in the liquid (1), for example water for injection purposes or physiological saline solution, present in the cylinder (101) of the cylinder/piston unit (100). For this purpose, the liquid (1) is to be pumped into the container (250).

In a first step, the unwinding banderole (280) is removed from the container region (221) and the container (250) is inserted into the container adapter (200) in the container insertion direction (7), cf. FIG. 2. The locking elements (223) are outwardly displaced. In this case, the tube (242) pierces, for example, the membrane cap (290) and optionally the closure membrane of the container (250) and enters the opening (253). Upon further insertion, the, for example, conically formed locking ring (248) jumps over the annular bead (326), with the annular bead (326) being elastically deformed. After the locking ring (248) is interlocked, the annular bead (326) is deformed back and assumes, with axial and radial play, its initial form above the, for example, horizontal locking lug (249), cf. FIG. 8.

In this exemplary embodiment, the axial length of the locking ring (248), which length is oriented in the longitudinal direction (5), is shorter than the axial length of the stopper attachment (325), and therefore, when the container (250) is inserted, the end surface (327) of the stopper (257) makes contact with the sliding surface (247). The stopper (257) is then displaced in the direction of the container interior (252) by means of the transfer tube (242) interlocked therewith. The transfer tube (242) is positioned in a sealing manner in the opening (253) under elastic deformation of the rings (246).

The, for example, manually actuated pushing movement of the container (250) is ended when the stopper (257) rests against the stops (225). The notches (259) engage in the locking elements (224). The membrane cap (290) is displaced along the transfer tube (242). When the container (250) is inserted, the air which is displaced in the process escapes through the slide recesses (228) of the container region (221), which slide recesses are covered in a sterile manner by the valve hose (229). In the illustration of FIGS. 3 and 9, the stopper (257) is displaced into the container interior (252) and hangs captively on the transfer tube (242). The transverse hole (245) protrudes out of the opening (253) in the direction of the container interior (252).

After the infiltrating of the transfer tube (242) into the cylinder interior (252), the cylinder interior (252) communicates with the cylinder interior (110) of the first cylinder/piston unit (100) via the connecting tube (242). The vacuum of the cylinder interior (252) draws the liquid out of the cylinder (101) of the cylinder/piston unit (100). As the cover covering the back of the cylinder (101) is a sterile filter membrane (119), the drawn-in piston (111) can follow the liquid (1) and enters into abutment with the cylinder floor (108). In the interior (252), the lyophilisate (2) is dissolved in the liquid (1). The dissolving process may be observed via the windows (226).

In a second step, the tear-off banderole (94) is removed as soon as the lyophilisate (2) has dissolved. The slots (57) of the triggering element (82) thus become visible. Now, the injector is positioned in such a way that the cylinder/piston unit (100) lies below the cylinder/piston unit (250). Afterwards, the newly produced solution (3) is to be pumped into the cylinder interior (110) through the transfer tube (242). For this purpose, the piston (261) is first released by radially pressing the locking elements (265) in. Owing to the residual vacuum, the piston stopper (267) is placed onto the surface of the solution (3). The solution (3) is now transferred by pumping to the cylinder interior (110) by applying a slight pressure to the piston (261). The piston stopper (267) is displaced in the direction of the opening (253). Here, it surrounds the stopper (257), which it receives, for example, in the cutout (269). The solution (3) pushes the piston (111) ahead of itself. Bubble-free filling of the cylinder interior (110) is checked in transmitted light via the windows (206). Generally, a small portion of the solution (3) is drawn back into the glass tube (251), so that, in addition, the piston (111) does not rest against the sterile filter membrane (119).

In a third step, the container adapter (200) is withdrawn with the cylinder/piston unit (250) from the housing (10). Nevertheless, the injector (4) remains secured, cf. FIG. 5.

Once the injector (4) has been placed with the cylinder/piston unit (100) onto the disinfected injection site, the block button (132) must be pressed in a last step, for example by the thumb of the hand holding the injector (4), in order to be able to move the triggering element (82) together with the triggering cap (81). The triggering element (82) can now be displaced in the direction of the cylinder/piston unit (100). During this process, the triggering element (82) slides on the outer wall (13) of the housing (10) linearly downward, i.e. in the direction of the injection site. The abutment surfaces (24) of the press rods (21) slip via the edge (85) and jump, under the force of the spring element (50), so as to release radially outward into the widening (83). The press rods (21) have bent resiliently outward and are now in their actual starting position. The press rods (21), which are now no longer deformed, release the piston actuating plunger (60), so that the piston slide (76) moves jerkily toward the sterile filter membrane (119) of the cylinder (101) under the action of the spring element (50). The sterile filter membrane (119) is pierced and the piston (111) is moved downward for draining the cylinder (101), cf. FIG. 6. The cylinder (100) is drained.

FIGS. 10 to 13 show a single-use injector (4) with an integrated two-chamber system (99), the second chamber (255) of which has a container (250) having a constant container volume.

The single-use injector (4) is constructed in a similar manner to the single-use injector (4) illustrated in FIGS. 1-6. However, the piston (111) has on its back a, for example central, frustoconical envelope-shaped recess (115) into which a pump rod (140) is screwed by means of a conical thread (141), cf. FIG. 12. The piston actuating plunger (60) has a, for example central, hole (63) through which the pump rod (140) passes with a high degree of play. The pump rod (140), which protrudes from the single-use injector (4), can be released from the piston (111) with the expenditure of little force.

A transfer tube (242), the main dimensions of which correspond for example to the main dimensions of the transfer tube (242) with a transverse hole (245), described in relation to the first exemplary embodiment, is integrated into the container adapter (200). The envelope surface (303) of the transfer tube (242) bears elastically deformable rings (246) which widen conically from the bottom to the top and the maximum external diameter of which is larger than the opening diameter of the container (250). The transfer tube (242) may be deformable in certain regions. It may consist, for example, of a two-component material with a deformation-resistant core and a soft, elastically deformable envelope.

The container adapter (200) has two slide apertures (228) which are closed, for example, by means of a valve hose (229) and are aligned with the The tube end (243) of the transfer tube (242) is embodied in the shape of an arrow with a sliding surface (247) surrounding the arrow (301).

The apex angle of the arrow (301) is, for example, 60 degrees. The back side (304) of the arrow tip (305), which side is upwardly directed here, comprises an annular plane which is oriented normally to the direction of the transfer tube (242).

The upper side of the stopper (257) sitting in the container opening (253) has a central recess (328) in the form of a blind hole. The depth of said recess (328) is greater than the length of the arrow (301) including the shaft (302). Below a shoulder (329), the recess (328) is, for example, of cylindrical design. The diameter of this region is larger than the maximum diameter of the arrow tip (305) and its depth is greater than the length of the arrow tip (305).

Above the shoulder (329)—the diameter of the shoulder (329) is larger than the diameter of the arrow shaft (302) and smaller than the largest diameter of the arrow tip (305)—the recess (328) is, for example, in the form of a conical section. It has an opening angle here of, for example, 60 degrees, with the notional cone apex being oriented in the direction of the container interior (252).

The container (250) is, for example, a glass bottle, or a lyophilisate bottle, with a waisted neck (259) and a flange edge (258). The flange edge (258) protrudes beyond the neck (259). However, the external diameter of the flange edge is smaller than the maximum external diameter of the container. The transition between the neck (259) and the cylindrical outer wall of the container (250) is rounded with a large radius corresponding, for example, to twice the thickness of the container wall. The container (250) is secured to the container adapter (200) via a cap (230) and a tear-off banderole (260).

In order to be able to use the single-use injector (4), the active substance (2), for example the lyophilisate, stored in the container (250) must be dissolved in the liquid (1), for example water for injection purposes or physiological saline solution, present in the cylinder (101) of the cylinder/piston unit (100). For this purpose, the liquid (1) is to be pumped into the container (250).

In a first step, the tear-off lug (281) is removed from the cap (230), while severing the perforation (282), and the cap (230) is withdrawn from the rear part of the container (250).

In FIG. 10, the container is closed by means of the aperture-free stopper (257). Both the container (250) and the openings of the transverse hole (245) of the connecting tube (242) may optionally be additionally closed by means of a membrane or by means of a membrane cap (290).

If appropriate, a resilient ring seal (217), which closes the joint between the container (250) and the inner wall of the container region (221) in a sterile manner, is located in an annular groove (216) of the container region (221).

Figure 12:
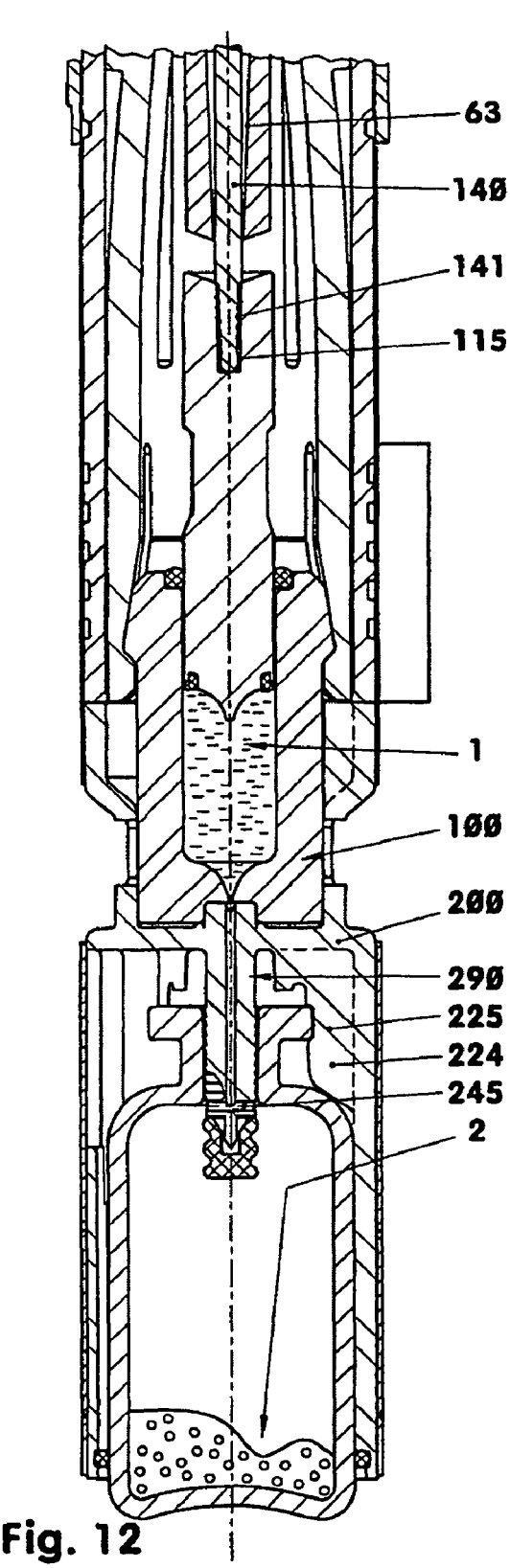
FIG. 12 shows FIG. 10 after insertion of the container.

In a second step, the container (250) is inserted into the container adapter (200). In this case, the container (250) slides forward on the inner wall of the container adapter (200) until its flange edge (258) rests against the stops (225), cf. FIGS. 11 and 12. At the same time, the locking rear grips (224) surround the back of the flange edge (258) and thus secure the front position of the container (250). During the forward movement, the container (250) has pressed the folding locking hooks (223) to the side and the locking hooks (224) interlock the container (250). FIG. 12 is a cross section of the container adapter (200) and of the inserted container (250).

According to the exemplary embodiments of FIGS. 10 and 11, on insertion of the container (250), the transfer tube (242) enters the opening (253) and the recess (328) of the stopper (257). In the process, the arrow tip (305) elastically deforms the shoulder (329) of the recess (328) and penetrates the region illustrated here below the shoulder (329). Upon further penetration of the arrow tip (305), the shoulder (329) is elastically deformed back such that a, for example, concentric aperture remains, said aperture surrounding the arrow shaft (302) and gripping behind the arrow tip (305). The stopper (257) is interlocked with the container adapter (200), cf. FIG. 13.

In this exemplary embodiment, the transfer tube (242) enters the recess (328) until the sliding surface (247) is placed on the upper side (332) of the stopper. The arrow tip (305) does not touch the floor (333) of the recess (328). Upon further insertion of the container (250), the container adapter (200) displaces the stopper (257) by means of the transfer tube (242) into the container interior (252). The transfer tube (242) now completely seals off the opening (253), cf. FIGS. 12 and 13.

Figure 13:
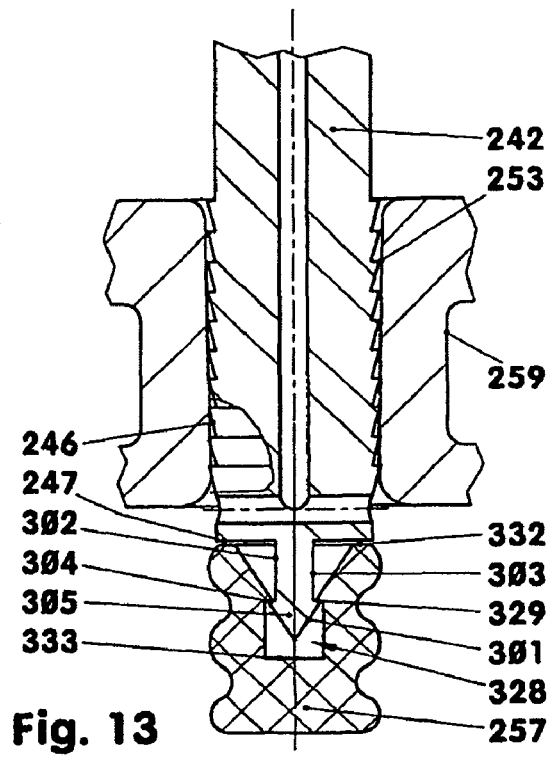
FIG. 13 shows a detail from FIG. 12.

As soon as the stopper (257) has left the opening (253), it slides downwards along the arrow shaft (302), in the illustration of FIG. 13, until the underside of the shoulder (329) rests on the back side (304) of the arrow tip (305). In this direction of movement, the deformation resistance of the shoulder (329) is of such a magnitude that the gravitational force of the stopper (257) causes only an insignificant deformation of the shoulder (329). The stopper (257) hangs undetachably on the arrow tip (305) which prevents the stopper from dropping down. The transverse hole (245) projects into the cylinder interior (252) and is located, for example, in the connection region of the bottle neck (259) such that said transverse hole is just free.

The cylinder interior (110) and the container interior (252) communicate via the transverse hole (245) and the hole (244) of the transfer tube (242). The locking hooks (224) prevent extraction of the container (250).

The excess pressure produced when the container (250) is inserted in the container region (221) escapes via the slide recesses (228) with, for example, partial raising of the valve hose (229), which also keeps the interior sterile. The slide recesses (228) and the valve hose (229) thus have the function of an excess pressure valve.

In a third step, the piston (111) is pushed into the cylinder (101) by means of the pump rod (140) and the liquid (1) is thus conveyed into the container interior (252) which is now under slight excess pressure. For this purpose, the pump rod (140) is in general held carefully between the index finger and the thumb of the operating hand.

The lyophilisate (2) is dissolved in the liquid (1). The dissolving process can be visually monitored, as the container (250) protruding from the container adapter (200) is transparent.

In a fourth step, the newly produced solution (3) is pumped back into the cylinder interior (110). For this purpose, the injector is held in such a way that the opening (253) of the container (250) points in the direction of gravity. The piston (111) is drawn into a rear position via the pump rod (140). Bubble-free filling is checked via the windows (206). A substantial emptying of the container (250) is ensured by the position of the transverse tube (245).

In a fifth step, the tear-off banderole (94) is separated all the way round from the main part (92) and from the adapter part (93) with the aid of a tear-off lug (95), for releasing the single-use injector. The slots (57) of the triggering element (82) become visible. The container adapter (200) is now withdrawn from the cylinder (101), for example downward.

In a last step, the injector is placed onto the disinfected injection site and the sleeve-like triggering element (82) is pushed downward—in the direction of the injection site. The press rods (21) bend resiliently outward into their actual starting position. In this case, the cams (22) slip outward into the widening (83) via the edge (85). The press rods (21), which are now no longer deformed, release the piston actuating plunger (60), so that the piston (111) moves jerkily downward, under the action of the spring element (50), for draining the cylinder (101). As the piston (111) moves forward, the piston friction is reduced intermittently, as the rearward sealing element does not abut in a braking manner as it passes the waisted piston region.

Figure 14:
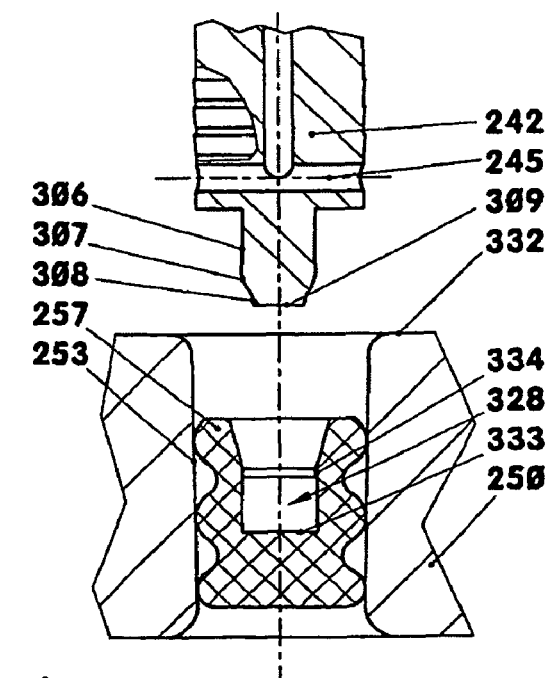
FIG. 14 shows the container adapter with a stopper.

FIG. 14 shows an alternative of the coupling between the container adapter (200) and the stopper (257). In this exemplary embodiment, the arrow tip (305) is replaced by a cylindrical shaft (306) which is tapered below an annular bead (307) in the form of a conical section. Upon displacement of the container (250), said shaft engages, for example, in a dome-shaped groove (334) of the stopper recess (328). In the exemplary embodiment illustrated, the end side (309) of the region (308) in the form of a conical section forms the sliding surface with which the transfer tube (242) pushes the stopper (257) out of the container opening (253). In the case of a container adapter (200) with a transfer tube (242) of shorter design, the sliding surface (247) is arranged around the transfer tube (242).

Combinations of the exemplary embodiments described are also conceivable.

List of Reference Numerals
1 Water for injection purposes, solvent
2 Lyophilisate, active substance, pharmaceutical composition
3 Injection solution
4 Single-use injector
5 Centre line of the injector, longitudinal direction
6 Triggering movement direction of (82), downward movement direction arrow
7 Container insertion direction
10 Housing, one-piece
13 Outer surface, cylindrical, outer wall
21 Press rods, support rods
22 Cams
23 Support surface
24 Abutment surface
28 Bending bar
31 Envelope region
33 Apertures
39 Floor
41 Fixing region for the cylinder/piston unit
42 Spring hook
43 Rear grip
50 Spring element, helical compression spring, spring energy store
57 Slots of (82)
59 Inner wall of (82)
60 Piston actuating plunger
62 Guide pin
63 Hole
73 Plunger plate
75 Collar surface, conical
76 Piston slide
80 Triggering unit
81 Triggering cap
82 Triggering element, triggering sleeve
83 Widening
84 Set-back flank
85 Edge, sharp-edged
90 Tamper-proof closure, banderole, securing element, adhesive label
92 Edge part, rear; label part
93 Edge part, front; label part
94 Tear-off banderole
95 Tear-off lug
96 Perforations, predetermined breaking points
99 Two-chamber system
100 Cylinder/piston unit, first, injector-side
101 Cylinder, injector-side
102 Locking ring
103 End face
104 Adhesive ring
105 Chamber
106 Hole, nozzle
107 Recess in the end face
108 Cylinder floor
110 Cylinder interior
111 Piston
112 Annular groove
114 Ring seal, seal
115 Recess in (111)
119 Sterile filter membrane
132 Block button
140 Pump rod
141 Conical thread
200 Container adapter
201 Adapter region
204 Shoulder, annular
206 Window, on both sides
211 Intermediate floor
213 Elevation
216 Annular groove
217 Ring seal
221 Container region, container receptacle
223 Locking elements, folding locking hooks
224 Locking elements, locking rear grips
225 Stops
226 Windows
228 Slide recesses
229 Valve hose
230 Cap
242 Transfer tube, connecting tube
243 Tube end
244 Hole, transfer tube hole
245 Transverse hole
246 Rings
247 Sliding surface
248 Locking ring 249 Locking lug
250 Cylinder/piston unit, second, container
251 Tube, glass tube, plastics material tube
252 Cylinder interior, container interior
253 Opening
255 Chamber
257 Stopper, resilient, rubber stopper
258 Flange edge
259 Notch, neck
261 Piston
262 Piston rod
263 Stopper carrier
264 Piston pressure plate
265 Locking elements
266 Collar
267 Piston stopper
268 Rubber ring, elastomer spring
269 Recess, cutout
280 Unwinding banderole
281 Tear-off lug
282 Perforation
290 Membrane cap
291 Wall region
292 Membrane, cap membrane
301 Arrow
302 Shaft
303 Envelope surface
304 Back side
305 Tip
306 Cylindrical shaft
307 Annular bead
308 Region in the form of a conical section
309 End side
321 Inner wall
322 Closure insert
324 Beads
325 Attachment, stopper attachment
326 Annular bead
327 End surface
328 Recess
329 Shoulder
332 Upper side of the stopper
333 Floor of (328)
334 Groove

What is claimed is:

1. In combination with a single-use injector (4) and two-chamber system (99), including at least a first chamber (105) being part of a cylinder/piston unit (100) having a cylinder interior (110) which can be received in the single-use injector (4) and a second chamber (255) being part of a container (250), the container (250) having an interior (252) and having at least one opening (253), the container (250) is closable at least temporarily by means of a stopper (257) and insertable in a container adapter (200) which is detachably mounted on the single-use injector (4), the improvement which comprises:

the container (250) upon partial insertion arrangement with the container adapter (200), the container adapter (200) closes the at least one opening (253) by displacing the stopper (257), the stopper (257) and the container adapter (200) upon partial insertion arrangement become interlocked non-detachably to each other, and the container (250) upon full insertion arrangement with the container adapter (200), the container adapter (200) having the stopper (257) affixed thereto, connects in fluid communication the cylinder interior (110) of the cylinder/piston unit (100) to the interior (252) of the container (250).

2. The combination according to claim 1, wherein the opening (253) of the container (250) is formed cylindrically or in the shape of a conical envelope, with, in the case of a formation in the shape of a conical envelope, the notional cone apex being arranged in the container interior (252).

3. The combination according to claim 1, wherein the container adapter (200) comprises a transfer tube (242) which is elastically deformable at least in certain regions, the transfer tube (242) has a longitudinal transfer tube hole (244) in the form of a blind hole.

4. The combination according to claim 3, wherein the inner wall (321) of the opening (253) is harder than the stopper (257) and the deformable region of the transfer tube (242).

5. The combination according to claim 3, wherein the transfer tube (242) interlocks with the stopper (257).

6. The combination according to claim 3, wherein the transfer tube (242) proximate a tube end (243) has a transverse hole (245), the transfer tube hole (244) opens into the transverse hole (245) penetrating the transfer tube (242).

7. The combination according to claim 6, wherein the transfer tube (242) proximate the tube end (243), has at least one bead-like, elastically deformable ring (246).

8. The combination according to claim 7, wherein the diameter of the at least one bead-like, elastically deformable ring (246) is larger than the diameter of the opening (253) of the container (250).

9. The combination according to claim 6, wherein the diameter of the transverse hole (245) corresponds to the diameter of the longitudinal blind hole (244).

10. The combination according to claim 6, wherein the tube end (243) of the transfer tube (242) has a central sliding surface (247) surrounded by a locking ring (248).

11. The combination according to claim 10, wherein the stopper (257) includes a conical attachment (325) including a peripheral annular bead (326) in lockable arrangement with the locking ring (248).

12. The combination according to claim 11, wherein the axial length of the locking ring (248) oriented in the longitudinal direction, is shorter than the axial length of the stopper attachment (325), whereby when the container (250) is inserted into the adapter (200), an end face (327) of the stopper (257) contacts the sliding surface (247) of the container adapter (200).

13. The combination according to claim 6, wherein the container adapter (200) further includes a pot-shaped membrane cap (290) in firm adherence to the transfer tube (242) proximate the tube end (243), the pot-shaped membrane cap (290) includes a cylindrical, elastically deformable wall region (291) and a cap membrane (292).

14. The combination according to claim 6, wherein the transfer tube (242) is longitudinally moveable to such an extent within the opening (253) of the container (250) that after infiltrating of the transfer tube (242) into the cylinder interior (252), the cylinder interior (252) fluidly communicates with the cylinder interior (110) of the cylinder/piston unit (100) via transverse hole (245).

15. The combination according to claim 6, wherein the container adapter (200) includes a container region (221), the container region (221) includes two groups of locking elements (223, 224) which are spaced apart in predetermined position for interlocking the container (250) to the adapter (200).

16. The combination according to claim 6, wherein the transfer tube (242) has a tube end (243) in the form of an arrow (301) with a shaft (302), the arrow (301) includes an arrow tip (305) having a back side (304) comprising an annular plane oriented normally to the direction of the transfer tube (242).

17. The combination according to claim 16, wherein the upper side of the stopper (257) has a central recess (328) having a depth greater than the length of the arrow (301) including the shaft (302), below a shoulder (329) of the central recess (328), the depth of the central recess (328) is greater than the length of the arrow (301) including the shaft (302), above the shoulder (329), the diameter of the shoulder (329) is smaller than the largest diameter of the arrow tip (305), whereby after the container (250) has been fully inserted into the container adapter (200) the arrow tip (305) is in lockable arrangement with the stopper (257).

18. The combination of claim 6, wherein the transfer tube (242) has a tube end (243) in the form of a cylindrical shaft (306), the cylindrical shaft (306) below a bead (307) has a lower conical section (308), the stopper (257) has a stopper recess (328) having a dome-shaped groove, whereby after the container (250) has been fully inserted into the container adapter (200) the cylindrical shaft (306) is in lockable arrangement with the stopper (257).

19. The combination according to claim 1, wherein the container adapter (200) has a sliding surface (247) for displacing the stopper (257).

* * * * *